United States Patent [19]

Hennart et al.

[11] Patent Number: 4,515,768
[45] Date of Patent: May 7, 1985

[54] INSECTICIDAL VAPORS-EMITTING COMPOSITION ON A PYRETHRINOID BASE

[75] Inventors: Claude Hennart, Seraincourt; René Blanc, Ligugé, both of France

[73] Assignee: Airwick Industries, Inc., Carlstadt, N.J.

[21] Appl. No.: 446,539

[22] Filed: Dec. 3, 1982

Related U.S. Application Data

[63] Continuation of Ser. No. 239,713, Mar. 2, 1981, abandoned.

[30] Foreign Application Priority Data

Mar. 5, 1980 [LU] Luxemburg ............... 82225

[51] Int. Cl.³ ............................ A01N 25/18
[52] U.S. Cl. ..................................... 424/40
[58] Field of Search ........................ 424/40

[56] References Cited

U.S. PATENT DOCUMENTS

| | | | |
|---|---|---|---|
| 3,224,973 | 12/1965 | Knapp | 252/49.8 |
| 3,270,091 | 8/1966 | Spivack | 260/932 |
| 3,281,505 | 10/1966 | Spivack | 260/953 |
| 3,367,870 | 2/1968 | Spivack | 252/49.8 |
| 3,723,615 | 3/1973 | Okuno | 424/40 |
| 3,819,823 | 6/1974 | Okuno | 424/40 |
| 4,037,352 | 7/1977 | Hennart et al. | 424/219 |
| 4,093,588 | 6/1978 | Spivack et al. | 260/45.8 R |
| 4,320,139 | 3/1982 | Takei et al. | 424/40 |

FOREIGN PATENT DOCUMENTS 1445813  8/1976  United Kingdom .

Primary Examiner—Delbert R. Phillips
Assistant Examiner—F. Moezie
Attorney, Agent, or Firm—Harry Falber

[57] ABSTRACT

Heat-stable composition, destined to emit insecticidal vapors by being heated, which contains at least one insecticidal substance of the family of pyrethrinoids, a stabilizer chosen from among the compounds defined by the chemical formula

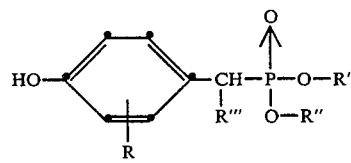

in which R represents one or two optional alkyl radicals containing one to twelve carbon atoms, R' and R", alike or different, represent each an alkyl radical containing one to eighteen carbon atoms, R' and R" together can represent a divalent saturated hydrocarbon group containing two to seven carbon atoms, and R''' represents a hydrogen atom or an alkyl radical containing one to seven carbon atoms; and, optionally, an adjuvant inert to the insecticide and chosen from among diluents, thickening agents, perfumes, synergists, colorants, repellants, solid supports and comburants.

6 Claims, No Drawings

INSECTICIDAL VAPORS-EMITTING COMPOSITION ON A PYRETHRINOID BASE

This is a continuation of application Ser. No. 239,713 filed on Mar. 2, 1981, now abandoned.

The present invention relates to compositions destined to emit insecticidal vapours and characterised by comprising a compound of the pyrethrinoid family and a novel stabiliser.

It is known to use insecticidal substances for the emission of vapours which are destined to destroy insects in the interior of inhabited localities. Thus far, there exists only one substance capable of giving off, at room temperature, vapours at a rate sufficient for obtaining a good insecticidal efficacy; this substance is an organophosphorus compound known by the name of Dichlorvos; its toxicity is, however, so high (DL 50 oral, acute in the vicinity of 55 mg/kg) that other insecticidal agents are preferred thereto. These are preferably in the pyrethrinoid family, as they are generally of little toxicity to man and to domestic animals. However, they require an elevated temperature to be evaporated and an effective concentration, and/or a very large evaporation surface.

In the French patent No. 2,322,546 of CIBA-GEIGY AG, there is described a device for emitting vapours of pyrethrinoids using a temperature between 65° and 90° C., but requiring an evaporation surface which can be of several square decimeters.

In the French patent No. 1,384,062 and in the Italian patent No. 713,459 of FUMAKILLA Ltd., there is described a device for emitting vapours of pyrethrinoids which comprises a surface of only a few square centimeters, but requiring a higher temperature. This type of device is marketed worldwide and uses a temperature generally between 150° and 160° C.

Yet, it is known that at temperatures in that range, the pyrethrinoids suffer a very rapid decomposition at a high degree; examples of this decomposition at temperatures in the range of 100° to 160° C. are given in the above-cited patents of FUMAKILLA Ltd (12 to 69% decomposition within 8 hours.

It has been attempted to remedy this situation by using stabilisers chosen from among diverse chemical classes. In several patents, there is contemplated the use of arylamines such as the phenylnaphthylamines (French application No. 2,226,112; U.S. Pat. Nos. 3,723,615, 3,819,823 and 3,934,023) or a derivative of paraphenylenediamine (Japanese application Nos. 73. 98,023 and 73. 98,024). It is known that these compounds are particularly toxic and, therefore, they are not being used in practice. In their place, there are preferred the substituted derivatives of phenol, such as 2-t-butyl-4-methoxyphenol (BHA) and 2,6-di-t-butyl-4-methylphenol (BHT) or the biphenols such as bis-(3-t-butyl-5-ethyl-2-hydroxy-phenyl)-methane and bis-(3-t-butyl-4-hydroxy-phenyl)-methane (French application Nos. 2,226,112 and 2,322,543; Japanese application Nos. 72.43,226 and 73.98,024; British Pat. Nos. 1,288,138, 1,295,039, 1,404,262, 1,427,309, 1,429,437 and 1,443,533). Unfortunately, the action of these phenolic compounds is often insufficient for protecting the pyrethrinoids at temperatures above 100° C. and often above 150° C.

There has also been contemplated the use of compounds of the family of benzodioxoles (Japanese application No. 73.99,328); the use of these compounds such as piperonylbutoxide, which is the most frequently used one, has been known for a long time, but it is necessary to use very large quantities of the same; this results in a noticeable cost increase and, moreover, the appearance of odours at the instant of placing such products in use.

It has now been found that certain hydroxybenzyl phosphonates permit obtainment of a stabilization of pyrethrinoids not only at temperatures between 150° and 160° C. but also at much more elevated temperatures, thereby enabling the use of pyrethrinoids which are much less volatile than those which are commonly used.

The hydroxybenzyl phosphonates are known compounds described in the French patent Nos. 1,320,375 and 2,253,025 and in U.S. Pat. No. 3,224,973. These compounds are known to have stabilizing properties permitting the protection of polymers such as caoutchouc, polyethylene and oils and fats utilizable as lubricants. However, they have never been used or contemplated for use for preventing the degradation of molecules which are as different from polymers or lubricants as are the insecticides of the pyrethrinoid family and, moreover, at particularly elevated temperatures.

It is conventional to employ in the insecticidal apparatus of the type referred to, allethrin or its resolved isomers, for these compounds possess a vapour tension which is relatively high in the pyrethrinoid family; nevertheless, they do not always possess an activity which is sufficiently lethal for certain insects, such as flies; and it is therefore interesting to be able to employ other compounds, alone or in mixtures, in order to augment this lethal effect and/or the velocity of action; but these other compounds requiring a much higher temperature, are rapidly decomposed by heat.

Furthermore, the use of a stabiliser of known type in order to try to delay this decomposition is not, in general, sufficient, probably because of its too rapid evaporation.

The invention remedies this drawback by enabling the preparation of compositions, based on pyrethrinoids, which are resistant to elevated temperatures for a prolonged period.

The invention thus relates to compositions destined to emit insecticidal vapours by heating, and comprising A—at least one insecticidal substance of the family of pyrethrinoids, B—optionally, an adjuvant inert to the substance A and selected from among diluents, thickening agents, perfumes, synergists, colorants, repellants, solid supports and comburants, which compositions are characterized in that they contain:

C—a stabiliser selected from among the compounds defined by the chemical formula

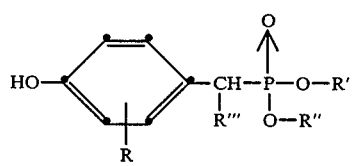

in which R represents one or two optional alkyl radicals containing one to twelve carbon atoms, R' and R" are alike or different and represent each an alkyl radical containing one to eighteen carbon atoms, R' and R" together can represent a divalent saturated hydrocarbon group containing two to seven carbon atoms; R''' represents a hydrogen atom or an alkyl radical containing one to seven carbon atoms.

As examples of the stabiliser C, there can especially be named the following compounds (these compounds are described in French patent Nos. 1,320,375 and 2,253,025 and in U.S. Pat. No. 3,224,973):

(4-hydroxy-benzyl)O,O-dibutyl phosphonate
(4-hydroxy-benzyl)O,O-butanediyl-(1,4)phosphonate
(4-hydroxy-benzyl)O,O-butanediyl-(1,2)phosphonate
(4-hydroxy-benzyl)O,O-pentanediyl-(1,5)phosphonate
(2-ethyl-4-hydroxy-benzyl)O,O-dibutyl phosphonate
1-(3-nonyl-4-hydroxy-benzyl)-butyl O,O-di-oct-2-yl phosphonate
(3-t-butyl-4-hydroxy-benzyl)O,O-dihexyl phosphonate
1-(3-amyl-4-hydroxy-phenyl)-ethyl O,O-diethyl phosphonate
(3-methyl-4-hydroxy-5-isopropyl-benzyl)O,O-diisopropyl phosphonate
(3-methyl-4-dodecyl-(3)-4-hydroxybenzyl O,O-diheptyl phosphonate
(3,5-di-t-butyl-4-hydroxy-benzyl)O,O-dioctadecyl phosphonate
(3-methyl-4-hydroxy-5-t-butyl-benzyl)O,O-dioctadecyl phosphonate
(3-methyl-4-hydroxy-5-t-butyl-benzyl)O,O-diisopropyl phosphonate
(3,5-dimethyl-4-hydroxy-benzyl)O,O-dibutyl phosphonate
(3,5-diethyl-4-hydroxy-benzyl)O,O-dibutyl phosphonate
(3,5-dipropyl-4-hydroxy-benzyl)O,O-dipropyl phosphonate
(3,5-diisopropyl-4-hydroxy-benzyl)O,O-diethyl phosphonate
(3,5-dibutyl-4-hydroxy-benzyl)O,O-dimethyl phosphonate
(3,5-diisobutyl-4-hydroxy-benzyl)O,O-diethyl phosphonate
(3,5-di-t-butyl-4-hydroxy-benzyl)O,O-dimethyl phosphonate
(3,5-di-t-butyl-4-hydroxy-benzyl)O-ethyl-O-methyl phosphonate
(3,5-di-t-butyl-4-hydroxy-benzyl)O,O-dipropyl phosphonate
(3,5-di-t-butyl-4-hydroxy-benzyl)O,O-diisopropyl phosphonate
(3,5-di-t-butyl-4-hydroxy-benzyl)O,O-dibutyl phosphonate
(3,5-di-t-butyl-4-hydroxy-benzyl)O-butyl-O-methyl phosphonate
(3,5-di-t-butyl-4-hydroxy-benzyl)O,O-diisobutyl phosphonate
(3,5-di-t-butyl-4-hydroxy-benzyl)O,O-di-t-butyl phosphonate
(3,5-di-t-butyl-4-hydroxy-benzyl)O,O-dipentyl phosphonate
(3,5-di-t-butyl-4-hydroxy-benzyl)O,O-diisopentyl phosphonate
1-(3-ethyl-4-hydroxy-5-isopropyl-phenyl)-ethyl O,O-dipentyl phosphonate
1-(3-dodecyl-4-hydroxy-5-octyl-phenyl)-pentyl O,O-didecyl phosphonate
1-[3-amyl-4-hydroxy-5-(heptyl-(2))-phenyl]-propyl O,O-diheptyl phosphonate
1-(3-butyl-4-hydroxy-5-hexyl-phenyl)2-ethyl-hexyl O,O-diundecyl phosphonate
(3,5-di-t-butyl-4-hydroxy-benzyl)O,O-ethanediyl-(1,2)phosphonate
(3,5-di-t-butyl-4-hydroxy-benzyl)O,O-propanediyl-(1,2)phosphonate
(3,5-di-t-butyl-4-hydroxy-benzyl)O,O-propanediyl-(1,3)phosphonate
(3,5-di-t-butyl-4-hydroxy-benzyl)O,O-butanediyl-(1,2)phosphonate
(3,5-di-t-butyl-4-hydroxy-benzyl)O,O-butanediyl-(1,3)phosphonate
(3,5-di-t-butyl-4-hydroxy-benzyl)O,O-pentanediyl-(1,5)phosphonate
(3,5-di-t-butyl-4-hydroxy-benzyl)O,O-(2,2-dimethyl-propanediyl-(1,3)phosphonate
(3,5-di-t-butyl-4-hydroxy-benzyl)O,O-(2-methylpentanediyl-(2,4))phosphonate
(3,5-di-t-butyl-4-hydroxy-benzyl)O,O-(2,2-dimethylpropanediyl-(1,2))phosphonate
(3,5-di-t-butyl-4-hydroxy-benzyl)O,O-(2-methylpropanediyl-(1,2))phosphonate
(3,5-di-t-butyl-4-hydroxy-benzyl)O,O-2(2,2-diethylpropanediyl-(1,3))phosphonate
(3,5-di-t-butyl-4-hydroxy-benzyl)O,O-2-methyl-2-propylpropanediyl-(1,3))phosphonate
(3,5-di-t-amyl-4-hydroxy-benzyl)O,O(2-methyl-2-ethyl-propanediyl-(1,3))phosphonate Preferred stabilisers are the (3,5-dialkyl-4-hydroxy-benzyl)phosphonates and, more in particular, the (3,5-di-t-butyl-4-hydroxy-benzyl)phosphonates.

The insecticidal substances A are all those known to the art-skilled to belong to the family of pyrethrinoids, regardless of their volatility. Among these substances, there can be cited, in particular, the esters formed between a cyclopropane-carboxylic acid such as the 2,2,3,3-tetramethylcyclopropane-carboxylic acid or the chrysanthemic acid, or 3-(2,2-butano- or 2,2-dibromo- or 2,2-dichloro- or 2,2-difluoro-vinyl)-2,2-dimethyl-cyclopropane-carboxylic acids in their racemic or resolved forms (d and/or l, cis and/or trans), and the following alcohols:

2-methyl-3-ethyl-4-oxo-cyclopent-2-enol
2-methyl-3-allyl-4-oxo-cyclopent-2-enol
2-methyl-3-methallyl-4-oxo-cyclopent-2-enol
2-methyl-3-methallyl-4-oxo-cyclopent-2-enol
2-methyl-3-crotyl-4-oxo-cyclopent-2-enol
2-methyl-3-(3-methyl-propen-2-yl)-4-oxo-cyclopent-2-enol
2-methyl-3-(2-chloro-allyl)-4-oxo-cyclopent-2-enol
2-methyl-3-(3-chloro-allyl)-4-oxo-cyclopent-2-enol
2-methyl-3-furfuryl-4-oxo-cyclopent-2-enol
1-phenyl-prop-2-ynol
1-(3-chloro-phenyl)-prop-2-ynol
1-(3-fluoro-phenyl)-prop-2-ynol
1-(3-trifluoromethyl-phenyl)-prop-2-ynol
1-(thien-2-yl)-prop-2-ynol
1-(fur-2-yl)-prop-2-ynol
4-phenyl-but-2-enol
4-(3-methyl-phenyl)-but-2-enol
4-(2-methyl-phenyl)-but-2-enol
4-(2,3-dimethyl-phenyl)-but-2-enol
4-(2-methoxy-phenyl)-but-2-enol
4-(2-chloro-phenyl)-but-2-enol
4-(3-chloro-phenyl)-but-2-enol
4-(2,3-dichloro-phenyl)-but-2-enol
4-(3-bromo-phenyl)-but-2-enol
4-phenyl-but-2-ynol
4-(fur-2-yl)-but-2-ynol
4-(thien-2-yl)but-2-ynol 5-methyl-5-hexen-2-ynol
5-methyl-hexa-2,5-dienol
5,6-dimethyl-5-hepten-2-ynol
2-methyl-benzyl alcohol
3-methyl-benzyl alcohol
4-methyl-benzyl alcohol
2,3-dimethyl-benzyl alcohol
2,4-dimethyl-benzyl alcohol
2,5-dimethyl-benzyl alcohol
2,6-dimethyl-benzyl alcohol
3,4-dimethyl-benzyl alcohol
3,5-dimethyl-benzyl alcohol
2,4,6-trimethyl-benzyl alcohol
4-allyl-benzylic alcohol
2,6-dimethyl-4-allyl-benzyl alcohol
4-methallyl-benzyl alcohol
4-(but-3-enyl)-benzyl alcohol
4-vinyl-benzyl alcohol
4-cyano-benzyl alcohol
4-trifluoromethyl-benzyl alcohol
4-nitro-benzyl alcohol
3-methyl-furfuryl alcohol
5-methyl-furfuryl alcohol
3,5-dimethyl-furfuryl alcohol
4,5-dimethyl-furfuryl alcohol
5-allyl-furfuryl alcohol
5-propargyl-furfuryl alcohol
2-methyl-fur-3-yl-methanol
2,5-dimethyl-fur-3-yl-methanol
2,4,5-trimethyl-fur-3-yl-methanol
5-allyl-fur-3-yl-methanol
2-methyl-5-allyl-fur-3-yl-methanol
2-methyl-5-propargyl-fur-3-yl-methanol
tetrahydrophthalimido-methanol
5-benzyl-fur-3-yl-methanol
5-(alpha-cyano-benzyl)-fur-3-yl-methanol
5-(alpha-methynyl-benzyl)-fur-3-yl-methanol
3-phenoxy-benzyl alcohol
3-phenoxy-(alpha-cyano)-benzyl alcohol
3-phenoxy-(alpha-methynyl)-benzyl alcohol.

These esters comprise in particular the substances known by the names of allethrin, bioallethrin, S-bioallethrin, cinerin, furetherin, dimethrin, benathrin, kadethrin, prothrin or furamethrin, proparthrin, tetramethrin, resmethrin, bioresmethrin, phenothrin, d-phenothrin, permethrin, biopermethrin, cypermethrin, bromethrin, decamethrin and fluorethrin.

Synergists, whenever, at least one of them is present in the composition, are selected from the benzodioxoles, the polychlorinated ethers and the N-alkyl norborn-5-ene-2,3-dicarboximides.

Suitable benzodioxoles are, for example, safrol, isosafrol, 5-cyano-benzo-1,3-dioxole, 5-ethynyl-benzo-1,3-dioxole, 5-hydroxymethyl-benzo-1,3-dioxole, 5-cyanomethyl-benzo-1,3-dioxole, 5,6-dichloro-benzo-1,3-dioxole, 5-chloro-6-cyano-benzo-1,3-dioxole, 5-bromo-6-cyano-benzo-1,3-dioxole, 5-chloro-6-cyanomethyl-benzo-1,3-dioxole, 5-chloro-6-hydroxybenzo-1,3-dioxole, 5-chloro-6-hydroxymethyl-benzo-1,3-dioxole, 5-chloro-6-ethynyl-6-benzo-1,3-dioxole.

Suitable polychlorinated ethers are, for example, 1,1,1,2,6,7,7,7-octachloro-4-oxa-heptane and 1,1,2,6,7,7-hexachloro-4-oxa-hepta-1,6-diene.

Suitable N-alkylnorbornene-2,3-dicarboximides are for example, those in which the alkyl radical is an isobutyl, sec-butyl, t-butyl, isopentyl, 2-methyl-butyl, isohexyl, 2-methyl-hexyl, 2-ethyl-butyl or isodecyl radical.

Suitable repellants are, for example, dialkyl succinates, malleates and fumartes, alkyl mandalates, N,N-dialkyl-benzamides and -toluamides, cyclopropane-carbonamides, 1-alkanoyl-hexahydrobenzofurans and 3,6-dioxadecyl alkanoates, citronellal and its dialkylacetals and alkylhexane-diols.

Diluants, whenever at least one of them is present in the composition, are chosen from among liquid or solid organic compounds having a dissolving power for the insecticidal substance. The used diluants preferably have a volatility in the vicinity of that of the insecticidal substance A.

Anyway, in order to permit the use of the compositions in certain applications, the invention does not exclude the presence therein of a diluent which is much more volatile, such as, for instance, dichloromethane, trichloroethane, trichloroethylene, perchloroethylene, acetone, butan-2-one, 4-methyl-pentan-2-one, methyl, ethyl, propyl, isopropyl, butyl, amyl acetates and other low-molecular weight aliphatic esters.

Among the diluents of low volatility, there can be cited in particular those chosen from among the following chemical families:

(1) monoesters formed between alkanols and monocarboxylated hydrocarbons such as, for instance, alkyl acetates such as those of hexadecyl or octadecyl, alkyl propionates such as those of hexadecyl and octadecyl, alkyl butyrates and isobutyrates such as those of dodecyl, tetradecyl, hexadecyl or octadecyl, alkyl hexanoates, alkyl octanoates, alkyl decanoates, alkyl laurates, undecanoates, undecenoates and myristates such as those of hexyl, octyl, decyl or dodecyl, alkyl palmitates and stearates such as those of propyl, butyl, isobutyl, amyl, hexyl or octyl, and alkyl benzoates, phenylacetates and phenylpropionates such as those of hexyl, octyl, decyl or dodecyl;

(2) diesters formed between alkanols and dicarboxylated hydro carbons such as, for instance, dialkyl adipates such as dioctyl adipate, dinonyl adipate, didecyl adipate and didodecyl adipate, dialkyl sebacates such as dibutyl sebacate, dipentyl sebacate, dioctyl sebacate and didecyl sebacate, dialkyl azelates such as dioctyl azelate and didecyl azelate, dialkyl phthalates such as dibutyl phthalate, dioctyl phthalate and didecyl phthalate, bis-undecyl phthalate, bis-dodecyl phthalate, bistridecyl phthalate, bis-tetradecyl phthalate and dicetyl phthalate;

(3) diesters formed between unsubstituted or alkyl-substituted phenols and dicarboxylated hydrocarbons such as, for example, diaryl phthalates such as di-phenyl phthalate and the dicresyl phthalates;

(4) diesters formed between alkyl-substituted or unsubstituted cycloalkanols and dicarboxylated hydrocarbons such as, for instance, dicyclohexyl phthalate, bis-(methylcyclohexyl)phthalates, bis-(trimethylcyclohexyl)phthalates and bis-(tetramethylcyclohexyl)phthalates;

(5) diesters formed between phenylalkanols and dicarboxylated hydrocarbons such as, for example, dibenzyl sebacate, dibenzyl azelate and bis-(phenylpropyl)sebacates;

(6) diesters formed between alkanediols and monocarboxylated hydrocarbons, such as, for instance, the diisobutyrate of 2,2,4-trimethyl-pentane-1,3-diol;

(7) triesters formed between alkyl-substituted or unsubstituted phenols and phosphoric acid, such as, for example, triphenyl phosphate, tris-(4-t-butyl-phenyl)phosphate and tricresyl phosphates;

(8) triesters formed between alkanols and phosphoric acid such as, for example, trioctyl phosphate, tridecyl phosphate and tridodecyl phosphate;

(9) polyalkyleneglycols such as, for example, polyethyleneglycols and polypropylene glycols;

(10) fatty alcohols such as, for instance, hexadecanol, octadecanol and octadecen-9-ol;

(11) fatty acids such as, for instance, lauric, myristic, palmitic, stearic and oleic acids;

(12) alkanes containing at least 18 carbon atoms, such as, for example, octadecane, eicosane, docosane and tetracosane, and their mixtures known by the names of vaseline oil, paraffin oil, heavy oil, gasoil, fuel oil, road oil, valve oil, mazout, vaseline, petrolatum, gatsch, paraffin, microwax, ozokerite and ceresin;

(13) alkanones containing at least eighteen carbon atoms, such as, for instance, caprinone, laurone, myristone, palmitone and stearone;

(14) alkenones containing at least eighteen carbon atoms, such as, for instance, heneicosa-1,20-dien-11-one and oleone.

Thickening agents are, for instance, metallic salts of fatty acid, such as aluminium or magnesium mono-, di- and tri-stearates, or salts of fatty acid and amine, such as dioleates of hexadecyl-amino propylene-amine, octadecyl-aminopropylene-amine or octadecenyl-aminopropyleneamine, or modified montmorillonites such as the ammonium salts of dimethyl-di-(high molecular weight-alkyl)-bentonite.

Solid supports, whenever at least one of them is present in the composition, are selected from organic powders, mineral powders and absorbent massic materials.

Organic powders can be chosen among all those known to the art-skilled, such as, for instance, starch, cereal flours, wood flour, sugars, dependent on what the composition is destined for.

Solid absorbant materials can be chosen among paper, cellulose cardboard composed of wood fibers, cereal fibers, alfalfa fibers, cotton fibers, waste of old paper, talcum fibers, glass fibers, wool fibers and/or polymeric fibers, and among terracotta, fritted alumina and unglazed porcelain.

The matter which constitutes the solid material may equally contain fillers chosen from among organic powders, mineral powders, pigments, colorants and binders.

The solid materials can adopt all known shapes such as those of plates and blocks.

Plates can be round, oval, square, rectangular, triangular or any kind of polygons; their total surface can be of only a few square centimeters or of several square decimeters, and their thickness can vary from 0.1 to 6 millimeters. Blocks can be cubic, prismatic, cylindrical, of elliptic or random polyhedric cross section; their total surface can vary from a few square centimeters to several square decimeters.

Comburants, whenever at least one of them is present in the composition, are destined to permit autocombustion of the latter and are chosen from among those known to an art-skilled person, such as, for instance, metallic or ammonium nitrates and nitrocellulose.

Preferably, the composition contains at least 5% by weight of the insecticidal substance A.

Preferably, the composition contains between 5 and 100 parts by weight of stabiliser C per 100 parts of the insecticidal substance A; better still, this proportion is comprised between 10 and 50 parts of stabiliser C.

When the composition does not comprise a solid support, it is prepared by simple mixing of the constituants without or with heating.

When the composition comprises a solid support such as an absorbant solid material, it is prepared by impregnating this material with a liquid mixture of the other constituents of the composition. The impregnation can be effected by pouring the liquid mixture on to the support or by soaking the latter with the liquid, soaking being possibly followed by draining; this operation can be mechanized by using, for instance, a dosifying pump or a spraying means of constant rate; a draining roller with adjustable pressure can also be used in order to permit retention of a desired proportion of the liquid; a centrifugal drain with adjustable speed can also be used for the same purpose. One industrially interesting mode of impregnation consists, for instance, in using ribbons of great length, being continuously impregnated and then cut off at desired dimensions. The impregnation can also be carried out by subjecting the solid support to vacuum in the presence of the liquid mixture.

The impregnation can also be effected automatically by a machine comprising one or more injection syringes and a conveqing belt causing to pass below them the solid supports to be impregnated. There can also be used, as mentioned hereinbefore, a solution of the liquid mixture in a volatile solvent which can then be evaporated.

When the composition comprises a solid support such as a powder and a comburant in order to obtain an autocombustible product, it is prepared by mixing the constituants with water or a volatile solvent so as to obtain a paste which is moulded or extruded and then subjected to drying according to a process known to the art-skilled, for instance, in an oven with hot air or in an evacuated vessel.

That the compositions according to the invention are of interest is illustrated by the following tests.

TEST 1

There are used the compositions 1-A and 1-B below which are obtained by impregnation of cellulose tablets of 34×21×3 millimeters with the liquid mixture of the other constituents:

|  | 1-A | 1-B |
|---|---|---|
| Bioresmethrin | 50 mg | 50 mg |
| Stabiliser (a) | — | 20 mg |
| Colorant (b) | 1 mg | 1 mg |
| Cellulose | 880 mg | 880 mg |

(a) (4-hydroxy-3,5-di-t-butyl-benzyl) O,O-diethyl phosphonate
(b) Organol Blue JN.

The thus impregnated tablets were placed each on an appropriate part of a commercial device destined for this use and comprising a heating resistor of 6800 ohms placed in a ceramic block having an upper heated surface of 35×20 mm.

The devices, with the tablets, were each placed in an apparatus capable of collecting all of the vapour emitted during operation, and are fed with A.C. of 220 volts during 3 hours, the temperature of the heated surface being 162° C.

At the end of this period, the amounts of undecomposed bioresmethrin present, on the one hand, in the tablets, and, on the other hand, in the collected vapours, were measured by analysis.

The results are summerised in the table below:

|  | 1-A | 1-B |
| --- | --- | --- |
| amount in the tablet | 17.5 mg | 48.0 mg |
| amount in the vapours | 1.5 mg | 1.5 mg |
| total undecomposed amount | 19.0 mg | 49.5 mg |
| decomposed amount | 31.0 mg | 0.5 mg |
|  | (62%) | (1%) |

TEST 2

The procedure of TEST 1 was followed, using the same device and the compositions 2-A and 2-B given below:

|  | 2-A | 2-B |
| --- | --- | --- |
| d-Phenothrin | 50 mg | 50 mg |
| Stabiliser (a) | — | 10 mg |
| Cellulose | 880 mg | 880 mg |

The device was connected to a source of A.C. of 250 volts permitting a temperature of 197° C. to be attained.

The amounts of undecomposed d-phenothrin found after 3 hours of operation permitted establishing the following table:

|  | 2-A | 2-B |
| --- | --- | --- |
| amount in the tablet | 5.0 mg | 27.5 mg |
| amount in the vapours | 15.0 mg | 19.5 mg |
| total undecomposed amount | 20.0 mg | 47.0 mg |
| decomposed amount | 30.0 mg | 3.0 mg |
|  | (60%) | (6%) |

TEST 3

The procedure of TEST 1 was followed, using the same device and the compositions 3-A and 3-B shown hereinafter:

|  | 3-A | 3-B |
| --- | --- | --- |
| Tetramethrin | 50 mg | 50 mg |
| Stabiliser (a) | — | 20 mg |
| Cellulose | 880 mg | 880 mg |

The device was connected to a source of A.C. of 250 volts permitting a temperature of 197° C. to be attained.

The amounts of undecomposed tetramethrin found after 3 hours of operation allowed establishing the following table:

|  | 3-A | 3-B |
| --- | --- | --- |
| amount in the tablet | 12.0 mg | 25.0 mg |
| amount in the vapours | 8.5 mg | 20.0 mg |
| total undecomposed amount | 20.5 mg | 45.0 mg |
| decomposed amount | 29.5 mg | 5.0 mg |
|  | (59%) | (10%) |

TEST 4

The procedure of TEST 1 is followed, using the same device and compositions 4-A and 4-B shown hereinafter:

|  | 4-A | 4-B |
| --- | --- | --- |
| Bioallethrin | 50 mg | 50 mg |
| Stabiliser (a) | — | 10 mg |
| Synergist (c) | 250 mg | 250 mg |
| Dioctyl sebacate | 250 mg | 250 mg |
| Colorant (b) | — | 7 mg |
| Cellulose | 880 mg | 880 mg |

(c) 1,1,1,2,6,7,7,7-octachloro-7-oxa-heptane.

The device was connected to a source of A.C. of 220 volts permitting attainment of a temperature of 162° C.

The amounts of undecomposed bioallethrin found after 3 hours of operation permitted establishing the following table:

|  | 4-A | 4-B |
| --- | --- | --- |
| amount in the tablet | 32 mg | 47 mg |
| amount in the vapours | 4 mg | 3 mg |
| total undecomposed amount | 36 mg | 50 mg |
| decomposed amount | 14 mg | 0 mg |
|  | (28%) | (0%) |

TEST 5

The procedure of TEST 1 was followed using the same device and the composition 5-A shown hereinafter:

| S-bioallethrin | 90 mg |
| --- | --- |
| Stabiliser (a) | 10 mg |
| Butyl stearate | 90 mg |
| Cellulose | 414 mg (d) |

(d) thickness of the tablets: 1.5 mm.

The device was fed A.C. so as to maintain a temperature of 162° C. during 8 hours, at the end of which the amounts of evaporated and residual S-bioallethrin were measured by analysis; the results were the following:

| Amount in tablet | 9.6 mg |
| --- | --- |
| Amount in vapours | 78.7 mg |
| total undecomposed amount | 88.3 mg |
| decomposed amount | 1.7 mg (1.9%) |

TEST 6

The procedure of TEST 1 was followed using the composition 6-A shown hereinafter obtained by impregnation of round cellulose tablets of 2 cm² surface and 1.25 mm thickness:

| S-bioallethrin | 20 mg |
| --- | --- |
| Stabiliser (a) | 1.25 mg |
| Cellulose | 125 mg |

The device is fed A.C. so as to maintain a temperature of 162° C. during 6 hours at the end of which the evaporated and residual amounts of S-bioallethrin were measured by analysis; the results were the following:

| | |
|---|---|
| Amount in the tablet | 0 mg |
| Amount in the vapours | 18.6 mg |
| Total undecomposed amount | 18.6 mg |
| Decomposed amount | 1.4 mg (7%) |

TEST 7

The procedure of TEST 1 was followed using a device having a heated upper surface of 36×40 mm and comprising two heating resistors of 6800 ohms each placed in a ceramic block and connected in parallel to a source of A.C. of 193 volts so as to raise the temperature of the surface to 160° C.

There were utilised, successively, the tablets 7-A to 7-D below, of dimensions of 35×30×1.5 mm.

| | 7-A | 7-B | 7-C | 7-D |
|---|---|---|---|---|
| d-phenothrin | 40 mg | 50 mg | 50 mg | 40 mg |
| stabiliser (a) | 10 mg | 10 mg | 5 mg | 2 mg |
| cellulose | 630 mg | 630 mg | 630 mg | 630 mg |

The tablets were placed, successively, during 8 hours on the heated part of the device at the end of which the amounts of evaporated and residual d-phenothrin were measured by analysis; the results were the following:

| | 7-A | 7-B | 7-C | 7-D |
|---|---|---|---|---|
| Amount in tablet | 25.0 mg | 30.0 mg | 28.0 mg | 17.0 mg |
| Amount in vapours | 14.3 mg | 16.7 mg | 18.2 mg | 15.9 mg |
| Total undecomposed amount | 39.3 mg | 46.7 mg | 46.2 mg | 32.9 mg |
| Decomposed amount | 0.7 mg (1.8%) | 3.3 mg (6.6%) | 3.8 mg (7.6%) | 7.1 mg (17.8%) |

TEST 8

The procedure of TEST 1 was followed using the same device and the compositions 8-A and 8-B given hereinafter:

| | 8-A | 8-B |
|---|---|---|
| Permethrin | 50 mg | 50 mg |
| Stabiliser (a) | — | 15 mg |
| Cellulose | 880 mg | 880 mg |

The device was connected to a source of A.C. so as to obtain a temperature of 260° C. on the heated surface, and the amounts of evaporated and residual permethrin were measured by analysis after three hours of operation; the results were the following:

| | 8-A | 8-B |
|---|---|---|
| Amount in tablet | 12.6 mg | 17.6 mg |
| Amount in vapours | 26.1 mg | 30.4 mg |
| total undecomposed amount | 38.7 mg | 48.0 mg |
| decomposed amount | 11.3 mg (22.6%) | 2.0 mg (4%) |

TEST 9

The procedure of TEST 1 was followed using the same device and the compositions 9-A, 9-B and 9-C shown below:

| | 9-A | 9-B | 9-C |
|---|---|---|---|
| Decamethrin | 50 mg | 50 mg | 50 mg |
| Stabiliser (a) | — | 10 mg | 20 mg |
| Cellulose | 880 mg | 880 mg | 880 mg |

The device was connected to a source of A.C. so as to attain a temperature of 260° C. on the heated surface, and the amounts of evaporated and residual decamethrin were measured after three hours of operation; the results were the following:

| | 9-A | 9-B | 9-C |
|---|---|---|---|
| Amount in tablet | 30 mg | 40 mg | 41 mg |
| Amount in vapours | 4 mg | 6.5 mg | 7 mg |
| total undecomposed amount | 34 mg | 46.5 mg | 48 mg |
| decomposed amount | 16 mg (32%) | 3.5 mg (7%) | 2 mg (4%) |

TEST 10

The procedure of TEST 1 is followed using a device having a heated supper surface of 36×40 mm and comprising two heating resistors of 6800 ohms each placed in a ceramic block, and connected in parallel to a source of A.C. of 193 volts so as to raise the temperature of the surface to 160° C.

There were used, successively, the tablets 10-A to 10-E defined hereinafter, of the dimensions 35×40×2.6 mm.

| | 10-A | 10-B | 10-C | 10-D | 10-E |
|---|---|---|---|---|---|
| Bioresmethrin | 50.0 mg | 50.0 mg | 50.0 mg | 50.0 mg | 50.0 mg |
| Stabiliser (a) | — | 4.0 mg | 2.5 mg | 5.0 mg | — |
| BHA (d) | — | — | — | — | 2.5 mg |
| BHT (d') | 2.5 mg | — | — | — | — |
| Cellulose | 1680 mg | 1680 mg | 1680 mg | 1680 mg | 1680 mg |
| Micromoles OH active | 11.3 | 11.2 | 7.0 | 14.0 | 13.9 |

(d) 2-t-butyl-4-methoxy-phenol
(d') 2,6-di-t-butyl-4-methyl-phenol.

The tablets were placed each, successively, on the heated part of the device during three hours at the end of which the amounts of evaporated and residual bioresmethrin were measured by analysis; the results were the following:

| | 10-A | 10-B | 10-C | 10-D | 10-E |
|---|---|---|---|---|---|
| Amount in tablet | 25.0 mg | 35.5 mg | 34.9 mg | 36.5 mg | 30.0 mg |
| Amount in vapours | 10.0 mg | 9.6 mg | 9.2 mg | 10.0 mg | 10.0 mg |
| Total undecomposed amount | 35.0 mg | 45.1 mg | 44.1 mg | 46.5 mg | 40.0 mg |
| Decomposed amount | 15.0 mg | 4.9 mg | 5.9 mg | 3.5 mg | 10.0 mg |

-continued

|  | 10-A | 10-B | 10-C | 10-D | 10-E |
| --- | --- | --- | --- | --- | --- |
|  | (30%) | (9.8%) | (11.8%) | (7%) | (20%) |

TEST 11

The procedure of TEST 10 was followed using the same device and the compositions 11-A to 11-E given hereinafter, of the dimensions 35×40×2.6 mm:

|  | 11-A | 11-B | 11-C | 11-D | 11-E |
| --- | --- | --- | --- | --- | --- |
| Tetramethrin | 50.0 mg | 50.0 mg | 50.0 mg | 50.0 mg | 50.0 mg |
| Stabiliser (a) | — | 8.4 mg | 5.0 mg | 10.0 mg | — |
| Bisphenol A (e) | 5.0 mg | — | — | — | — |
| Bisphenol B (e') | — | — | — | — | 5.0 mg |
| Cellulose | 1680 mg | 1680 mg | 1680 mg | 1680 mg | 1680 mg |
| Micromoles OH actif | 23.7 | 23.6 | 14.0 | 28.1 | 29.4 |

(e) bis-(3,5-di-t-butyl-4-hydroxy-phenyl) methane
(e') bis-(2-hydroxy-3-t-butyl-5-methyl-phenyl) methane The device was connected to a source of A.C. of 250 volts permitting a temperature of 197° C. to be attained.

The tablets were each placed, successively, on the heated part of the device during 3 hours at the end of which the evaporated and residual amounts of tetramethrin were measured by analysis; the results were the following:

|  | 11-A | 11-B | 11-C | 11-D | 11-E |
| --- | --- | --- | --- | --- | --- |
| Amount in tablet | 25.0 mg | 29.5 mg | 29.0 mg | 29.9 mg | 20.0 mg |
| Amount in vapours | 8.5 mg | 11.2 mg | 10.5 mg | 11.6 mg | 11.0 mg |
| Total undecomposed amount | 33.5 mg | 40.7 mg | 39.5 mg | 41.5 mg | 31.0 mg |
| Decomposed amount | 16.5 mg | 9.3 mg | 10.5 mg | 8.5 mg | 19.0 mg |
|  | (33%) | (18.6%) | (21%) | (17%) | (38%) |

The results of TESTS 10 and 11 show that the compositions according to the invention enable obtainment of a better stability and, hence, a better yield of the insecticidal substance, by using a stabiliser as provided by the invention rather than a stabiliser chosen from among those known to the art-skilled.

TEST 12

The procedure of TEST 1 was followed by using the same device, and the composition 12-A below:
d-Phenothrin 50 mg
Piperonylbutoxyde 250 mg
Cellulose 880 mg.

The device was connected to a source of A.C. of 250 volts permitting a temperature of 197° C. to be attained.

The evaporated and residual amounts of d-phenothrin were measured by analysis after three hours of operation; the results were the following:

| Amount in the tablet | 40.0 mg |
| --- | --- |
| Amount in the vapours | 2.5 mg |
| Total undecomposed amount | 42.5 mg |
| Decomposed amount | 7.5 mg (15%). |

These results are to be compared with those obtained in TESTS 2 and 7. They show the compositions according to the invention are stabler than those obtained by employing a compound of the benzodioxole family, even when using it at a rate of 500%.

What is claimed is:

1. A composition which emits insecticidal vapors upon being heated comprising at least 5%, by weight, of an insecticidal substance of the family of pyrethrinoids susceptible to thermal decomposition and O,O-diethyl (3,5-ditert-butyl-4-hydroxybenzyl)phosphonate as a stabilizer for retarding the decomposition thereof;
   said stabilizer being present in a concentration of from about 5-100 parts, by weight, for each 100 parts of insecticidal substance.

2. Composition according to claim 1, characterised in that the insecticidal substance is an ester derived from an acid selected from the group consisting of chrysanthemic acid, 2,2,3,3-tetraethyl-cyclopropane-carboxylic acid 2,2-dimethyl-3-(2,2-butano-vinyl)-cyclopropane-carboxylic acid, 2,2-dimethyl-3-(2,2-dibromo-vinyl)-cyclopropane-carboxylic acid and 2,2-dimethyl-3-(2,2-dichloro-vinyl)-cyclopropane-carboxylic acid in their racemic or resolved d or l, cis or trans forms.

3. Composition according to claim 1, characterised in that the insecticidal substance is selected from the group consisting of allethrin, bioallethrin, S-bioallethrin, cinerin, furethrin, dimethrin, benathrin, kadethrin, prothrin, furamethrin, proparthrin, tetramethrin, resmethrin, bioresmethrin, phenothrin, d-phenothrin, permethrin, biopermethrin, cypermethrin, bromethrin, decamethrin and fluorethrin.

4. Composition according to claim 1, characterised in that it additionally contains a synergist selected from the group consisting of benzodioxoles, polychlorinated ethers and N-alkyl-5-norbornene-2,3-dicarboximides.

5. Composition according to claim 1, characterised in that the proportion of stabiliser is comprised between 10 and 50 parts of stabiliser for 100 parts of insecticidal substance.

6. The composition of claim 1 which is present on an absorbant solid support substrate.

* * * * *